United States Patent [19] [11] Patent Number: 4,789,629
Baker et al. [45] Date of Patent: Dec. 6, 1988

[54] METHOD AND DEVICE FOR COLLECTING AND TESTING FOR FECAL OCCULT BLOOD

[75] Inventors: Josefina T. Baker, Cupertino, Calif.; Joseph F. Pagano, Paoli, Pa.; Ronald J. Schoengold, San Jose, Calif.

[73] Assignee: SmithKline Beckman Corporation, Philadelphia, Pa.

[21] Appl. No.: 934,035

[22] Filed: Nov. 24, 1986

[51] Int. Cl.$^4$ .................. G01N 33/53; G01N 33/72
[52] U.S. Cl. ............................... 435/7; 128/638; 128/759; 206/204; 422/56; 422/58; 422/61; 435/28; 435/810; 436/66; 436/808; 436/904
[58] Field of Search ............ 435/7, 28, 810, 188, 435/805; 436/66, 904, 810, 808; 422/61, 56, 57, 58; 128/638, 759, 749; 206/204, 569, 472, 473

[56] References Cited

U.S. PATENT DOCUMENTS

| 3,966,006 | 12/1976 | Pagano | 23/253 |
| 4,273,741 | 6/1981 | Levine | 128/638 |
| 4,427,769 | 1/1984 | Adlercreutz et al. | 435/7 |
| 4,645,743 | 2/1987 | Baker et al. | 436/66 |

Primary Examiner—Robert J. Warden
Assistant Examiner—Florina B. Hoffer
Attorney, Agent, or Firm—Joseph A. Marlino; Stuart R. Suter; Alan D. Lourie

[57] ABSTRACT

A method and slide for collecting and testing fecal occult blood which permits multiple analyses of a single fecal sample. The slide contains a pocket-like member on a portion of the inside front cover of the slide. An absorbent insert is disposed in the pocket. When the cover is in a closed position the pocket overlies the fecal smear on the specimen viewing sheet and the insert can be removed from the pocket. This design permits an analysis to be done on the specimen receiving sheet of the slide together with a second confirmatory test on the insert.

6 Claims, 2 Drawing Sheets

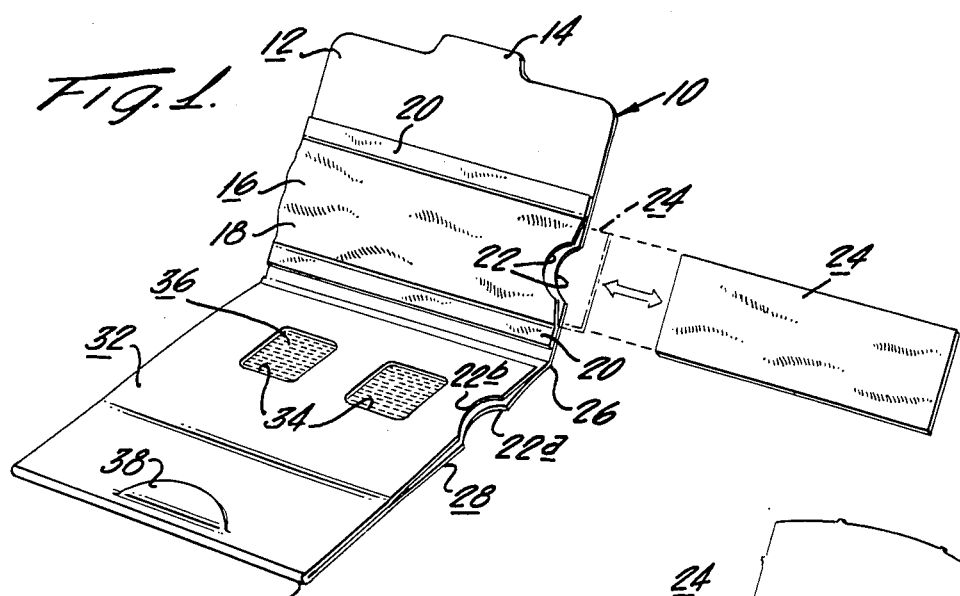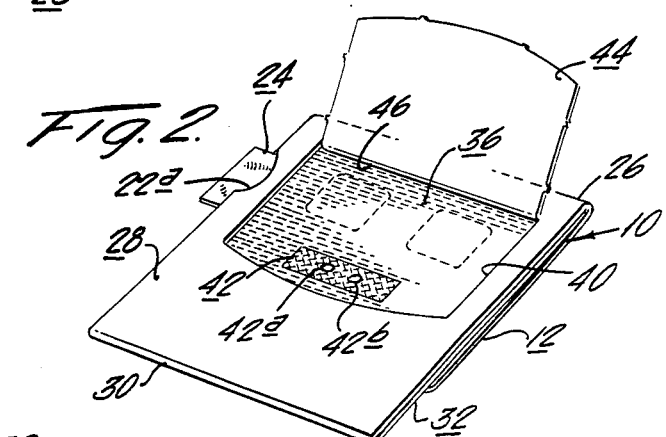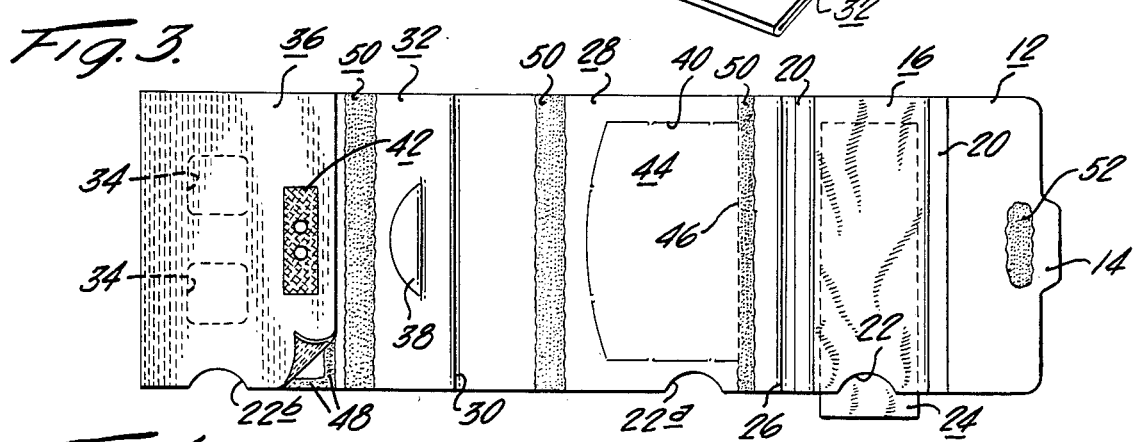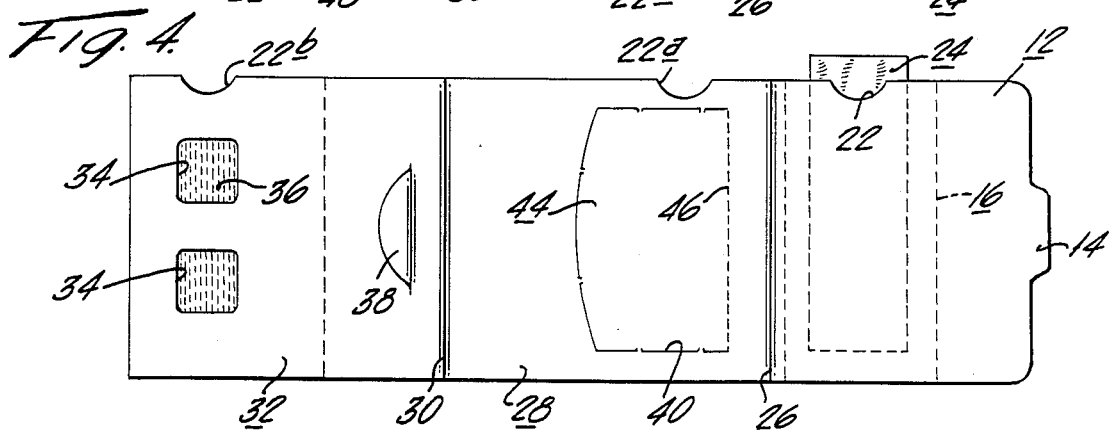

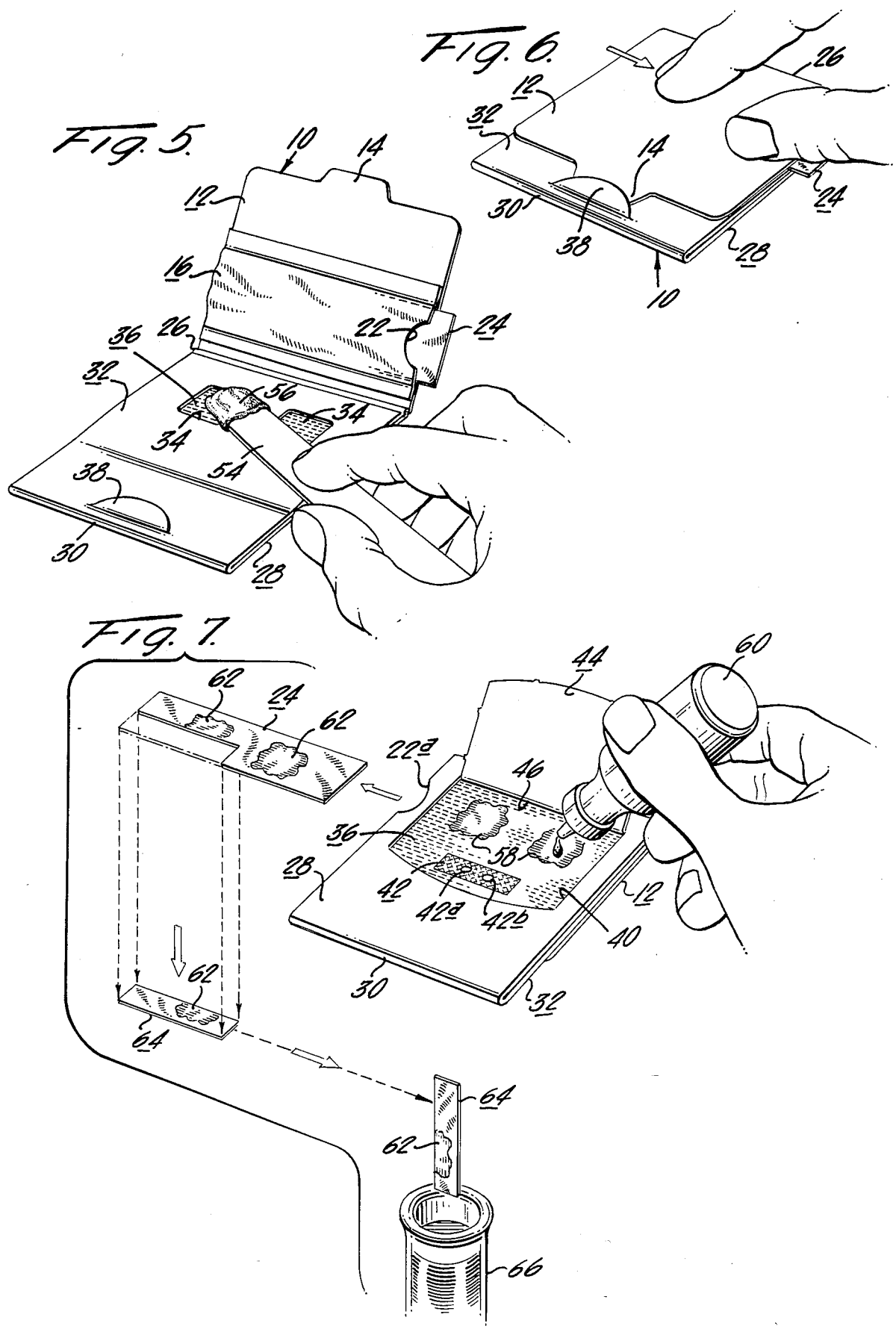

METHOD AND DEVICE FOR COLLECTING AND TESTING FOR FECAL OCCULT BLOOD

This invention relates to a convenient method and device for collecting and detecting occult blood in fecal matter. More particularly, this invention relates to a collection and test device that permits multiple analyses of a single fecal sample. The device of this invention can be used to collect, transport and carry out a variety of analyses in a single fecal sample at two different test sites of the device. The device can be employed in the privacy of one's home and is convenient to use.

Specimen slides and procedures for detecting occult blood in fecal matter are well known. Typically, in the case of a test for occult blood in feces, a sample of fecal matter is smeared on the specimen test sheet which has been treated with guaiac. A developing solution, such as a peroxide solution, is applied to the opposite side of the sheet. If blood is present in the fecal matter, the guaiac reaction will color the paper blue. This procedure is disclosed in U.S. Pat. No. 3,966,006.

One of the disadvantages associated with this test is that false positive results can occur, i.e., the positive non-hemoglobin interfering substances in the fecal matter such as peroxidases, various foodstuffs, drugs, and animal heme, which can be a result of meat in the diet, can give a positive result.

The above disadvantage may be minimized by the use of immunological tests which are specific for human hemoglobin. The enzyme immunoassay (EIA) for the detection of human hemoglobin in feces is known to the art. Briefly, the EIA test is a reaction between an antibody and an antigen (hemoglobin). The hemoglobin is reacted with a specific anti-human hemoglobin antibody and attached to the solid phase. This antibody-antigen complex is then reacted with anti-human hemoglobin which is conjugated to alkaline phosphatase. The enzymatic activity of the resulting complex bound to the solid phase is then quantified. A color intensity is measured instrumentally and the absorbence is directly related to the amount of human hemoglobin (antigen) in the sample. A typical EIA assay for fecal human hemoglobin is disclosed in U.S. Pat. No. 4,427,769.

However, the EIA assay described above also has its disadvantages. Human hemoglobin in fecal samples degrades with time. The degradation occurs with loss of antigenicity which results in falsely reduced values when employing the EIA assay. In brief, the immunoassay test specific for human hemoglobin requires that the hemoglobin retains its structural integrity. It has been discovered that guaiac is one component that has a deleterious effect on the stability of human hemoglobin.

A known device and method for conducting an immunoassay for fecal human hemoglobin is also disclosed in U.S. Pat. No. 4,427,769. On this device (Fecatest), the fluids from the fecal sample are passed through a guaiac impregnated filter paper onto an absorbent material before conducting an EIA assay. The following studies were conducted after storing fecal samples containing human hemoglobin in the Fecatest device.

Three fecal samples containing human blood were applied to and stored in the Fecatest device up to nine days and then analyzed by FECA-EIA Labsystems assay. The results, i.e., color intensity measured at an absorbency of 405 nm are set forth below in Table 1.

TABLE 1

| SAMPLE | R.T. STORAGE DURATION, DAYS | | | |
|---|---|---|---|---|
| No. | 0 | 1 | 3 | 9 |
| 1 | 2.05 | 0.48 | 0.13 | 0.00 |
| 2 | 1.07 | 0.31 | 0.00 | 0.00 |
| 3 | 2.24 | 0.89 | 0.00 | 0.00 |

The above data clearly show the rapid degradation of hemoglobin with time. Virtually no color is seen on Day 3 on all samples.

When the same fecal samples were applied to the sampling device of the present invention and stored up to nine days, a surprising improvement in the stability of hemoglobin was observed. The EIA kit supplied by Labsystems as noted above was also employed to analyze these samples. The results are set forth in Table 2.

TABLE 2

| SAMPLE | R.T. STORAGE DURATION, DAYS | | | |
|---|---|---|---|---|
| No. | 0 | 1 | 3 | 9 |
| 1 | 2.62 | 1.71 | 1.56 | 0.86 |
| 2 | 2.36 | 2.58 | 1.10 | 0.26 |
| 3 | 2.06 | 1.40 | 0.96 | 0.32 |

Color is visible in all samples even after 9 days of storage at room temperature.

It is thus desirable that samples analyzed immunologically for human hemoglobin be protected from excessive contact with guaiac. The present invention minimizes guaiac contamination of the sample that may have to be analyzed immunologically for human hemoglobin.

It is therefore an object of this invention to provide a testing device and method which minimizes the guaiac contamination of the fecal sample that is to be analyzed immunologically for human hemoglobin.

It is a further object of this invention to provide a test device and method which permits the multiple analyses of a single fecal sample at two different test sites on the device.

Briefly, this invention consists of an improved test device for fecal occult blood having a guaiac treated specimen receiving sheet between a front panel and a rear panel with openings in each of the panels and pivotal covers to cover those openings, similar to the slide described in U.S. Pat. No. 3,996,006. A portion of the inside front cover has a pocket-like member and an absorbent insert which is retained within the pocket. The design is such that when the front cover is closed a portion of the insert disposed in the pocket-like member is exposed beyond the closure line of the cover. This enables one to withdraw the absorbent insert from the pocket with the cover remaining closed. After removal the insert which absorbs the fecal fluid through the pocket can be sectioned for a confirmatory assay, such as an immunological assay. Further, when the cover is in a closed position the pocket containing the insert overlies the openings in the front panel which contain the fecal sample.

A detailed description and better understanding of this invention can be had by referring to the accompanying drawings which show a preferred embodiment of the present invention.

FIG. 1 is a perspective view of the test device of this invention as viewed from the front with the cover in an open position showing the pocket-like member and absorbent insert;

FIG. 2 is a perspective view of the device of FIG. 1 as viewed from the rear showing rear flap open exposing the testing surface including the control area and a portion of the insert extending from the closed slide;

FIG. 3 is a plan view of a blank prior to folding for preparing a slide in accordance with this invention;

FIG. 4 is a bottom plan view of the blank shown in FIG. 3;

FIG. 5 is a perspective view of the slide as viewed from the front in an opened mode about to receive a fecal sample to be tested and showing the insert in the pocket on the inside of the front cover;

FIG. 6 is a perspective view of the slide in a closed mode prior to testing demonstrating pressure being applied to the cover to insure contact of the pocket with the fecal sample;

FIG. 7 is a perspective view of the rear panel of the slide showing a developing solution being applied to the testing surface including the control area, after the absorbent insert has been removed, and the subsequent confirmatory testing of the fecal stain on the insert for human hemoglobin.

Referring to FIGS. 1 and 2 testing device 10 has a front panel 32, a rear panel 28, and a cover 12. The front panel has a pair of adjacent openings 34. A sheet of absorbent paper 36 is placed between the front and rear panel as viewed in insert 40 of the rear panel. Sheet 36 is impregnated or printed with a reagent such as, for example guaiac. A portion of sheet 36 has a control area 42 having a positive monitor 42a and a negative monitor 42b. Rear panel 28 is provided with a flap 44 which is secured to the panel by perforated hinge 46 and when open reveals the testing area 40.

The inside of cover 12 has a pocket-like member 16 which comprises a rectangular sheet 18 having the consistency of thin translucent filter paper such as, for example, a tea bag. An absorbent insert 24 is retained within the pocket. The design is such that when the cover is closed the pocket overlies openings 34 and a portion of the insert 24 disposed in the pocket is exposed beyond the closure line. This enables one to withdraw the absorbent insert from the pocket with the cover remaining closed. A means for grasping the insert when the cover is closed is provided by a notch 22, 22a and 22b cut through the slide. The insert which absorbs fecal fluid through the pocket can be sectioned for a confirmatory assay, such as an immunological assay. The insert is free of guaiac.

To form the completed slide as shown in FIGS. 1 and 2, the panels of the blanks comprised of paper or Cardboard as viewed in FIGS. 3 and 4 are folded along crease line 30 to bring panels 32 and 28 together and hold them together principally by the adhesive strips 50. Cover 12 is now hinged about crease 26 and secured to panel 32 by a spot of adhesive 52 such as; for example, glue. The cover may also be secured by co-acting tab 14 with lock 38.

To use the slide, the patient separates cover 12 from panel 32 and applies with applicator 54 a thin smear of specimen from a portion of his stool 56 on sheet 36 through opening 34 as illustrated in FIG. 5. As viewed in FIG. 6 after the fecal sample has been transferred to the slide and the front cover is closed pressure may be applied to the cover to insure contact of the pocket with the fecal sample and staining of the insert. As it will also be noted from FIG. 6 a portion of the insert 24 is exposed beyond the closure line of the cover. The patient returns the slide to his physician or a laboratory for analysis. As illustrated in FIG. 7 the absorbent insert 24 which was housed in the pocket is removed from the slide and set aside while the guaiac test is developed. The technician then pulls flap 44 free of panel 28 and opens it outwardly. Through the opening thus made a developing solution 60 such as hydrogen peroxide is applied to guaiac treated sheet 36 at stained area 58. The developing solution is also applied to control area 42 to cover positive and negative monitors 42a and 42b. The results are then observed, i.e., a blue color denotes a positive test.

If the guaiac test is positive the insert which is free of guaiac and was set aside is used to conduct a second confirmatory test, such as an immunological test specific for human hemoglobin. The insert containing fecal stains 62 can be cut into strips 64. The strips can be placed in tube 66 containing reagents to elute the fecal matter for an EIA assay. Alternatively, the insert may be punched out instead of cut into strips.

The main advantage of this invention, therefore, is that in one single collection two separate membranes, i.e., the specimen receiving sheet and the absorbent insert, receive the components of the fecal sample and can be individually and independently tested. The fecal matter is placed in direct contact with the specimen receiving sheet which contains guaiac. The fluid from the fecal sample passes through the pocket member and is collected on the insert which is free of guaiac. This design permits for both the standard test for fecal occult blood which depends on the hemoglobin catalyzed oxidation of guaiac and a confirmatory test such as an immunological assay specific for human hemoglobin in which the fecal sample should be relatively free of any contact with guaiac. Further, these tests can be conducted without disturbing or removing the fecal matter from the slide.

Another advantage of the device of this invention is that the construction is not air-tight and enough absorbent material is provided so that drying and aeration of the sample is facilitated. This is necessary to minimize microbial growth that may further degrade hemoglobin or other analytes of interest. Known sampling and testing devices that are kept tightly closed do promote growths of black and moldy spores.

This invention also permits improved sample selection. The technician is presented with a relatively big absorbent insert containing the fecal components for an EIA assay. The technician is able to view the absorbent insert and punch or cut out samples, for EIA assay from areas of highest fecal concentration, i.e., the most stained areas. Such a selection is not possible with prior art devices where pre-cut discs absorb whatever amount of fecal fluid that comes through a guaiac containing membrane.

The above embodiments are illustrative and are not intended to be limiting.

What is claimed is:

1. In an occult blood specimen test slide having a front panel, a rear panel, said front panel having one or more openings, sheet means carrying a test reagent between the front and rear panels underlying each of said openings a hinged cover configured to overlie a portion of the front panel and said openings and flap means in the rear panel opposite said openings and pivotable to expose the underside of the sheet, the improvement comprising a pocket-like member attached to a portion of the inside of said hinged cover and an absorbent insert disposed in said pocket whereby when the cover is in a closed mode, the pocket is positioned to overlie the openings of the front panel and the insert which has a portion exposed beyond the closure line of the cover can be slidably removed from the pocket, said pocket-like member having a consistency which permits filtration of a specimen fluid onto said insert.

2. The test slide of claim 1 wherein the test reagent is guaiac.

3. A method for determining the presence of fecal occult blood with the specimen test slide of claim 1 which comprises:
 (a) smearing fecal matter onto the reagent sheet through an opening of the front panel;
 (b) closing the front cover of the test slide whereby the pocket is overlying the opening and the insert has a portion exposed beyond the closure line;
 (c) removing the insert which contains fecal fluids which passed through the pocket from the fecal matter;
 (d) opening the rear cover and applying a developing solution to the reagent sheet at the corresponding opening in the rear panel, and
 (e) conducting a second confirmatory test on the insert, said insert being free of guaiac.

4. The method of claim 3 in which the confirmatory test is an immunological assay specific for human hemoglobin.

5. The method of claim 3 wherein the reagent is guaiac.

6. A test kit for collecting and testing fecal occult blood which comprises the device of claim 2 and a developing solution which reacts with said guaiac to color the sheet blue.

* * * * *